United States Patent [19]

Hammond et al.

[11] Patent Number: 5,147,800
[45] Date of Patent: Sep. 15, 1992

[54] HOST EXPRESSING NGOAIII RESTRICTION ENDONUCLEASE AND MODIFICATION METHYLASE FROM NEISSERIA

[75] Inventors: Alan W. Hammond; Deb K. Chatterjee, both of Gaithersburg, Md.

[73] Assignee: Life Technologies, Inc., Gaithersburg, Md.

[21] Appl. No.: 535,021

[22] Filed: Jun. 8, 1990

[51] Int. Cl.$^5$ .................. C12N 1/21; C12N 15/74
[52] U.S. Cl. .................. 435/252.3; 435/320.1; 435/196; 435/871
[58] Field of Search .................. 435/188, 320.1, 172.3, 435/252.3, 871, 196

[56] References Cited

PUBLICATIONS

Hammond et al., Nucleic Reid Res. vol. 17(16): 6750, 1989.
Norlander et al., J. Bact. Feb. 1981, p. 788.
USB Corp. Catalogue 1987, p. 19.
Davies Clin. Microbiol. Res. Apr. 1989, p. 578.
Chien et al., Cloning and Characterization of a Restriction and Modification System from Neisseria gonorrhoeae Strain MS11, Abstracts of the ASM Annual Meeting, p. 213 (1988).
Roberts, R. J., Restriction Enzymes and Their Isoschizomers, Nucleic Acids Research, 17, Supp., pp. 347–387.
Sullivan, K. M. and Saunders, J. R., Sequence Analysis of the NgoPII Methyltransferase Gene from Neisseria gonorrhoeae P9 . . . , Nucleic Acids Research, 16(10): 4369–4387, (1988).
Sullivan et al., Characterization of DNA Restriction and Modification Activities in Neisseria Species, FEMS Microbiology Letters, 44:389–393 (1987).
Wilson, G. G., Cloned Restriction-Modification Systems-A Review, Gene, 74:281–289 (1988).
Duff et al., Gene 1 74:227–228 (1988).
Hammond et al., Nucleic Acids Research 17(8):3320 (1989).
Lunnen et al., Gene 74:25–32 (1988).
Piekarowicz et al., Nucleic Acids Research 19(8):1831–1835 (1991).
Piekarowicz et al., Gene 74:93–97 (1988).
Piekarowicz et al., Nucleic Acids Research 16(13):5957–5972 (1988).
Ritchot et al., Gene 86:103–106 (1990).
Wilson, G. G., Trends In Genetics 4(11):314–318 (1988).
Szomolanyi et al., Gene 10:219–225 (1980).
Kiss and Baldauf, Gene 21:111–119 (1983).
Janulaitis et al., Gene 20:197–204 (1982).
New England Biolabs, 1988–1989 Catalog, pp. 19 and 29.

Primary Examiner—Richard A. Schwartz
Assistant Examiner—John L. Leguyader
Attorney, Agent, or Firm—Sterne, Kessler, Goldstein & Fox

[57] ABSTRACT

The present invention is directed to recombinant hosts which contain and express various Type II restriction endonuclease and/or modification methylase genes. In particular, the present invention is concerned with the cloned restriction endonucleases, NgoAIII and NgoAI, which recognize and cleave within or near the double-stranded DNA sequence, 5' CCGCGG 3' and 5' PuGCGCPy 3', respectively. Also provided in this invention are cloned modification methylase genes corresponding to said restriction endonucleases. This invention is further concerned with a cloned modification methylase, M.NgoAII. One source of these enzymes is Neisseria gonorrhoeae, although other microorganisms may be used to isolate the restriction endonuclease isoschizomers and modification methylase isoschizomers of this invention.

10 Claims, 1 Drawing Sheet 5,147,800

HOST EXPRESSING NGOAIII RESTRICTION ENDONUCLEASE AND MODIFICATION METHYLASE FROM NEISSERIA

FIELD OF THE INVENTION

This invention is directed to recombinant hosts expressing restriction endonuclease and modification methylase genes from the genus Neisseria. This invention is specifically directed to the recombinant hosts and their cloning vectors which contain the genes coding for the restriction endonuclease NgoAI and its corresponding methylase M.NgoAI, the restriction endonuclease NgoAIII and its corresponding methylase M.NgoAIII, or the modification methylase M.NgoAII. This invention is also directed to cloned restriction endonuclease and modification methylase isoschizomers of these enzymes.

BACKGROUND OF THE INVENTION

Restriction endonucleases are a class of enzymes that occur naturally in prokaryotic and eukaryotic organisms. When they are purified away from other contaminating cellular components, restriction endonucleases can be used in the laboratory to cleave DNA molecules into precise fragments. This property enables DNA molecules to be uniquely identified and to be fractionated into their constituent genes. Restriction endonucleases have proved to be indispensable tools in modern genetic research. They are the biochemical "scissors" by means of which genetic engineering and analysis are performed.

Restriction endonucleases act by recognizing and binding to particular sequences of nucleotides (the "recognition sequence") along the DNA molecule. Once bound, they cleave the molecule within, or to one side of, this sequence in both strands. Different restriction endonucleases have affinity for different recognition sequences. About 100 kinds of different endonucleases have so far been isolated from many microorganisms, each being identified by the specific base sequence it recognizes and by the cleavage pattern it exhibits. In addition, a number of restriction endonucleases, called restriction endonuclease isoschizomers, have been isolated from different microorganisms which in fact recognize the same recognition sequence as those restriction endonucleases that have previously been identified. These isoschizomers, however, may or may not cleave the same phosphodiester bond as the previously identified endonuclease.

In nature, restriction endonucleases play a protective role in the welfare of the microbial cell. They enable the microorganism to resist infection by foreign DNA molecules like viruses and plasmids that would otherwise destroy or parasitize them. They achieve this resistance by scanning the lengths of the infecting DNA molecule and cleaving them each time that the recognition sequence occurs. The DNA cleavage that takes place disables many of the infecting genes and renders the DNA susceptible to further degradation by nonspecific exonucleases.

A second component of microbial protective systems are the modification methylases. Modification methylases are complementary to their corresponding restriction endonucleases in that they recognize and bind to the same recognition sequence. Modification methylases, in contrast to restriction endonucleases, chemically modify certain nucleotides within the recognition sequence by addition of a methyl group. Following this methylation, the recognition sequence is no longer bound or cleaved by the restriction endonuclease. The microbial cell modifies its DNA by virtue of its modification methylases and therefore is completely insensitive to the presence of its endogenous restriction endonucleases. Thus, endogenous restriction endonuclease and modification methylase provide the means by which a microorganism is able to identify and protect its own DNA, while destroying unmodified foreign DNA.

The combined activities of the restriction endonuclease and the modification methylase are referred to as the restriction-modification system. Three types of restriction-modification systems have been identified that differ according to their subunit structure, substrate requirements and DNA cleavage. Specifically, Type-I and Type-III restriction systems carry both modification and ATP-requiring restriction (cleavage) activity in the same protein. Type-II restriction-modification systems, on the other hand, consist of a separate restriction endonuclease and modification methylase, i.e., the two activities are associated with independent proteins.

Type II restriction endonucleases are endodeoxyribonucleases which are commonly used in modern genetic research. These enzymes recognize and bind to particular DNA sequences and once bound, cleave within or near this recognition sequence. Phosphodiester bonds are thereby hydrolyzed in the double stranded DNA target sequence, i.e., one in each polynucleotide strand. Type-II restriction endonucleases can generate staggered breaks within or near the DNA recognition sequence to produce fragments of DNA with 5' protruding termini, or DNA fragments with 3' protruding termini. Other Type-II restriction endonucleases which cleave at the axis of symmetry, produce blunt ended DNA fragments. Therefore, Type-II restriction endonucleases can differ according to their recognition sequence and/or the location of cleavage within that recognition sequence.

Type-II restriction endonucleases are frequently used by the genetic engineers to manipulate DNA in order to create novel recombinant molecules. Specific Type-II restriction endonucleases are known for numerous DNA sequences, but there is still a need to provide new Type-II restriction endonucleases. These new enzymes will add to the list of indispensable tools needed for modern genetic research.

SUMMARY OF THE INVENTION

The present invention is directed to recombinant hosts which contain and express various Type II restriction endonuclease and/or modification methylase genes. This invention is further directed to a process for obtaining these enzymes and the use thereof.

In particular, the present invention is concerned with the cloned restriction endonuclease, NgoAIII, which recognizes the palindromic sequence:

5' CCGC ↓ GG 3'

GG ↑ CGCC 5' and cleaves the sequence between the second C and G residues from the 5' end producing a two-base 3' extension. The cloned modification methylase corresponding to this endonuclease is called M.NgoAIII.

In addition, this invention relates to the cloned restriction endonuclease, NgoAI, and its corresponding modification methylase (M.NgoAI) which recognize the palindromic sequence 5' PuGCGCPy 3'

3' PyCGCGPu 5'.

Furthermore, the present invention is directed to a recombinant host expressing the modification methylase, M.NgoAII which recognizes and chemically modifies the palindromic sequence

5' GGCC 3'

3' CCGG 5'.

DEFINITIONS

Figure 1:
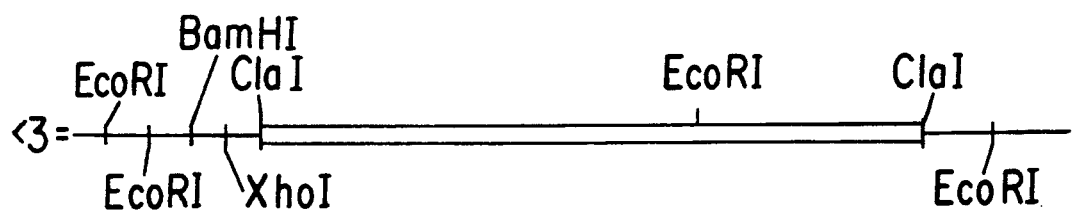
FIG. 1 shows a simplified restriction map of plasmid DNA, 61X3. This plasmid contains and expresses the genes which encode for NgoAIII and M.NgoAIII.

In the description that follows, a number of terms used in recombinant DNA technology are extensively utilized. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vector, and into which DNA may be spliced in order to bring about its replication and cloning. The cloning vector may further contain a marker suitable for use in the identification of cells transformed with the cloning vector. Markers, for example, are tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences.

Restriction endonuclease isoschizomer. A restriction endonuclease isoschizomer is a term used to designate a group of restriction endonucleases that recognize and bind to the same recognition sequence but are isolated from different microbial sources. Restriction endonucleases isoschizomers may or may not cleave in the exact location as the restriction endonuclease with which it is being compared.

Modification methylase isoschizomer. A modification methylase isoschizomer is a term used to designate a group of modification methylase that recognize the same recognition sequence but are isolated from different microbial sources. Modification methylase isoschizomers may or may not chemically modify the same nucleotides within the recognition sequence as the modification methylase with which it is being compared.

Recognition sequence. Recognition sequences are particular sequences which restriction endonucleases and modification methylase recognize and bind along the DNA molecule. Recognition sequences are typically four to six (and in some cases eight) nucleotides in length with a two fold axis of symmetry.

Recombinant host. Any prokaryotic or eukaryotic microorganism which contain the desired cloned genes on an expression vector or cloning vector.

Host. Any prokaryotic or eukaryotic microorganism that is the recipient of a replicable expression vector or cloning vector.

Promoter. A DNA sequence generally described as the 5' region of a gene, located proximal to the start codon. At the promoter region, transcription of an adjacent gene(s) is initiated.

Gene. A DNA sequence that contains information encoding for a polypeptide or protein, and as used herein, includes the 5' and 3' ends.

Structural gene. A DNA sequence that is transcribed into messenger RNA that is then translated into a sequence of amino acids characteristic of a specific polypeptide. Typically the first nucleotide of the first translated codon is numbered +1, and the nucleotides are numbered consecutively with positive integers through the translated region of the structural gene and into the 3' untranslated region. The numbering of nucleotides in the promoter and regulatory region 5' to the translated region proceeds consecutively with negative integers within the 5' nucleotide next to the first translated nucleotide being numbered −1.

Operably linked. As used herein means that the promoter controls the initiation of the expression of the polypeptide encoded by the structural gene.

Expression. Expression is the process by which a structural gene produces a polypeptide. It involves transcription of the gene into messenger RNA (mRNA) and the translation of such mRNA into polypeptide(s)

DETAILED DESCRIPTION OF THE INVENTION

This invention is directed to recombinant hosts which express genes encoding for Type II restriction endonucleases including NgoAIII or NgoAI. NgoAIII recognizes the palindromic sequence 5' CCGCGG 3', and cleaves between the second C and G residues from the 5' end, producing a two-base 3' extension. The double-stranded recognition site of NgoAIII is thus characterized as follows:

5' CCGC ↓ GG 3'

3' GG ↑ CGCC 5'

(wherein G represents deoxyguanosine and C represents deoxycytidine. NgoAI recognizes and cleaves within or near the double-stranded palindromic sequence:

5' PuGCGCPy 3'

3' PyCGCGPu 5'

(wherein Py represents deoxythymidine (T) and deoxycytidine (C), and Pu represents deoxyguanosine (G) and deoxyadenosine (A)).

This invention is also directed to recombinant hosts which express the corresponding modification methylase genes of NgoAIII and NgoAI. M.NgoAIII recognizes and binds to the same recognition sequence as NgoAIII while M.NgoAI recognizes and binds to the sequence recognized by NgoAI. Rather than cleaving the DNA, these methylase chemically modify certain nucleotides within the recognition sequence by addition of a methyl group, thus making the modified sequence resistant to cleavage with its corresponding restriction endonuclease.

This invention is further concerned with a recombinant host which express a gene encoding for the modification methylase, M.NgoAII. M.NgoAII recognizes and chemically modifies, by addition of a methyl group, the double-stranded palindromic sequence

5' GGCC 3'

3' CCGG 5'.

Also provided in this invention are recombinant hosts which express genes encoding for isoschizomers of the restriction endonuclease and modification methylase of the present invention (NgoAII, M.NgoAIII, NgoAI, M.NgoAI and M.NgoAII).

I. Isolation of the Genes Encoding Restriction Endonucleases and Modification Methylases of the Present Invention or Isoschizomers thereof The restriction endonucleases and their corresponding modification methylases of the present invention (NgoAIII, M.NgoAIII, NgoAI, M.NgoAI, and M.NgoAII) may be obtained from any species of *Neisseria gonorrhoeae*. Genes encoding isoschizomers of these enzymes can be obtained from any genus including, but not limited to, Arthrobacter, Bacillus, Citrobacter, Enterobacter, Escherichia, Flavobacterium, Haemophilus, Klebsiella, Micrococcus, Neisseria, Nocardia, Pseudomonas, Salmonella, and Streptomyces. The preferred genus to isolate isoschizomers of the modification methylases and restriction endonucleases of the present invention is Neisseria. The genus Neisseria are gram negative cocci occurring in pairs or in masses and are aerobic or facultatively anaerobic. These organisms may be found in the oropharynx or nasopharynx and the genitourinary tract of humans and animals.

Nomenclature for naming the restriction endonucleases are in accord with the proposal of Smith et al., *J. Mol. Biol.* 81: 419-423 (1973). Briefly, the first letter "N" of NgoAIII designates the genus Neisseria while the lower case letters "go" designates the species, *gonorrhoeae*.

Any strain of Neisseria capable of producing restriction endonuclease isoschizomers of NgoAIII or NgoAI—or modification methylase isoschizomers of M.NgoAIII, M.NgoAI or M.NgoAII—can be used for the purpose of this invention. For example, *Neisseria meningitidis, Neisseria sicca, Neisseria mucosa, Neisseria lactamica, Neisseria ovis, Neisseria subflava,* and *Neisseria flavescens* may be used to obtain the genes expressing the restriction endonuclease isoschizomers of NgoAIII or NgoAI. Any species of Neisseria may also be used to isolate the genes coding for the modification methylase isoschizomers of M.NgoAIII, M.NgoAIV or M.NgoAII.

The preferred species in the present invention for obtaining the genes encoding enzymes of the present invention (NgoAIII, M.NgoAIII, NgoAI, M.NgoAI, and M.NgoAII) is *Neisseria gonorrhoeae* as described in the examples.

II. Cloning and Expressing the Genes Encoding for the Restriction Endonucleases and Modification Methylases of the Present Invention or Isoschizomers thereof NgoAIII, M.NgoAIII, NgoAI, M.NgoAI and M.NgoAII are preferably obtained by isolating the genes encoding for the enzymes from *Neisseria gonorrhoeae* and then cloning and expressing them. It is understood in this invention that genes coding for isoschizomers of the restriction endonucleases and modification methylases of the present invention may be obtained from any microorganism including the genus Neisseria by using the recombinant techniques described herein.

DNA molecules which code for NgoAIII, M.NgoAIII, NgoAI, M.NgoAI, and M.NgoAII, or isoschizomers thereof, can be recombined into a cloning vector and introduced into a host cell to enable the expression of the restriction endonuclease or modification methylase by that cell. DNA molecules may be recombined with vector DNA in accordance with conventional techniques, including blunt-ended or staggerended termini for ligation, restriction receptor molecule digestion to provide appropriate termini, filling in of cohesive ends as appropriate, alkaline phosphatase treatment to avoid undesirable joining, and ligation with appropriate ligases.

a. Hosts for Cloning and Expressing

The present invention encompasses the expression of the desired restriction endonuclease or modification methylase in prokaryotic cells. Preferred prokaryotic hosts include bacteria such as *Escherichia coli,* Bacillus, Streptomyces, Pseudomonas, Salmonella, Serratia, Neisseria etc. The most preferred prokaryotic host is *E. coli*.

It has been found that *E. coli* has several mechanisms (restriction systems) for identifying foreign DNA and destroying it. This can be a significant problem in cloning experiments, resulting in reduced recovery of the desired sequences. In particular, it has been found that *E. coli* contains restriction systems that degrade DNA when it is methylated, either cytosine residues or adenine residues. Specifically, the well known methylcytosine-specific systems include mcrA (rglA), and mcrB (rglB). The methyladenine-specific restriction system has been designated mrr. Thus, the preferred host for cloning and expressing the genes encoding for the enzymes of the present invention is an *E. coli* host in which these restriction systems have been inactivated through mutation or loss.

Bacterial hosts of particular interest in the present invention include *E. coli* K12 strain K802 (mcrA, mcrB, $r_k^-$ and $m_k^-$), *E. coli* K12 DH5αMCR (F−, endo A1, hsdR17[$r_k^-$, $m_k^+$], supE44, thi−1, λ−, recA1, gyrA96, relA1, φ80dlacZ, ΔM15, ΔmcrB, mcrA, mrr) and DH10B (F−, araD139 Δ (ara, leu) 7697, ΔlacX74, galU, galK, mcrA, Δ(mrr hsd RMS mcrB), rpsL dor. φ80 dlac Z ΔM15, endA1, nupG, recA1). The prokaryotic host must be compatible with the replicon and control sequences in the cloning vector.

b. Methods for Cloning and Expression

NgoAIII, M.NgoAIII, NgoAI, M.NgoAI, and M.NgoAII or isoschizomers thereof are preferably obtained by isolating the genes coding for the enzymes and then cloning and expressing them. Wilson, "Cloned restriction-modification system—a review," *Gene* 74:281-289 (1988), describes four techniques for isolating and cloning restriction endonuclease and modification methylase. The four methods reviewed include (1) subcloning of natural plasmids; (2) selection based on phage restriction; (3) selection based on vector modification involving methylation protection; and (4) multistep isolation. Any one of these four methods can be used for isolating and cloning the genes encoding for the enzymes of the present invention or isoschizomers thereof.

The preferred method according to this invention is vector modification technique, i.e., methylation protection. Methylation protection involves digestion of a plasmid library with the restriction enzyme to be cloned so that only plasmids whose sequences are modified, because of the presence of the methylase, will produce transformants in a suitable host. This selection has worked well to clone endonuclease and methylase genes together as well as methylase genes alone (Szomolanyi et al., 1980; Janulaitis et al., 1982; Walder et al., 1983; Kiss and Baldanf, 1983; and Wilson, 1988).

Specifically, selection based on modification requires that the vector used to construct the plasmid library contain at least one recognition site (recognition sequence) corresponding to the modification methylase to be cloned. Clones that contain the modification gene on the plasmid vector will methylate their own plasmid DNA, provided that the modification methylase is expressed in the host used. Thus, plasmid DNA isolated from such clones will therefore be resistant to digestion in vitro by the corresponding restriction endonuclease.

It is known that linear plasmid DNA will transform competent cells at a much lower frequency than uncleaved circular DNA. It therefore follows that restriction endonuclease digestion of plasmid library followed by transformation into a suitable host will result in the selection survival of methylase-encoding clones. Moreover, if the methylase-encoding clone also contains the corresponding restriction gene, then such clones will also provide the means for expressing and harvesting the restriction enzyme itself.

Restriction genes and their corresponding modification genes are usually closely linked in the DNA of many bacteria. This being the case, selection for methylase-containing cells can be used as a simple and reliable method for selectively co-isolating methylase and endonuclease clones. In brief, selection of methylase-carrying clones from plasmid libraries which also contain DNA fragments coding for the corresponding restriction genes frequently results in the isolation of clones that carry both the modification methylase gene and the corresponding restriction endonuclease gene. Methylase-selection is therefore an indirect way of selecting a restriction endonuclease clone.

The preferred methods to clone and express the genes of the present invention (NgoAIII, M.NgoAIII, NgoAI, M.NgoAI, and M.NgoAII) or isoschizomers thereof, are described in the following steps:

1. The DNA of the bacterial species to be cloned is purified.

2. The DNA is digested partially with a convenient restriction endonuclease.

3. The resulting fragments are ligated into a cloning vector, such as pCP13 (Darzins, A. et al., *J. Bacteriol.* 159:9-18 (1984)), and the mixture is used to transform an appropriate host cell, such as *E. coli*.

4. The DNA/cell mixture is plated on antibiotic media selective for transformed cells. After incubation, the transformed cell colonies are pooled and an aliquot of this cell suspension is grown to create the cell library.

5. The recombinant plasmids are purified in toto from the cell library to make a plasmid library.

6. The plasmid library is then digested to completion in vitro with the restriction enzyme whose corresponding methylase gene is sought. Exonuclease and/or phosphatase may also be added to the digestion to enhance the destruction of non-methylase plasmids.

7. The digested plasmid DNA is transformed into *E. coli* and transformed colonies are again obtained by plating on antibiotic plates. Individual colonies are picked and analyzed for the presence of the modification methylase.

8. If clones are found to express modification methylase, they are further analyzed for the simultaneous expression of the restriction endonuclease.

9. Methylase screening may be performed by: (a) The recombinant plasmid DNA molecule of the clone may be purified and exposed in vitro to the selecting restriction endonuclease to establish that it is resistant to digestion. Provided that the plasmid vector carries several sites for that endonuclease, resistance indicates modification rather than mutational site loss.

(b) The total chromosomal DNA of the clone may be purified and exposed to the selective restriction endonuclease. If the clone carries the methylase gene, the bacterial chromosome should be fully methylated and, like the plasmid, should be found to be resistant to digestion.

(c) The cell extract from the clone may be prepared and assayed in vitro for methylase activity (methylase protection and radioactive labelling).

10. Restriction endonuclease screening may be carried out as follows:

(a) The cell extract from the clone may be prepared and assayed in vitro for its ability to digest substrate DNA, such as Ad-2. Cleavage of Ad-2 DNA indicates the presence of cloned restriction endonuclease.

(b) The cells themselves may be tested in vivo for their ability to resist phage infection. Resistance to phage infection indicates the presence of the restriction endonuclease.

The restriction endonuclease used to selectively digest the plasmid library in step 6 is usually the same as that encoded by the restriction-modification system to be cloned. Occasionally, the selective restriction endonuclease can be used to clone identical restriction-modification systems from other microorganisms, i.e., to clone exact isoschizomers of the prototype enzyme (the first example isolated). It has been shown, for example, that HaeIII was used to select the isoschizomeric restriction-modification system of BsuRI (Kiss et al., *Nucleic Acid Res.* 13:6403-6421 (1983)). Both HaeIII and BsuRI cleave at the same location within the recognition sequence, 5'GG↓CC3'. Selection for isoschizomeric restriction-modification systems can be accomplished, provided that the modification methylase isoschizomer to be cloned can cross-protect against cleavage with the selective endonuclease.

Applicants have used commercially available prototype restriction endonucleases to select isoschizomeric restriction-modification systems that recognize and cleave the same recognition sequence as the endonuclease used to select these clones. Applicants have shown, for example, that SstII can be used to select recombinant hosts expressing NgoAIII and M.NgoAIII; HaeII can be used to isolate recombinant hosts expressing NgoAI and M.NgoAI; and HaeIII can be used to select recombinant hosts expressing M.NgoAII.

Although the steps outlined above are the preferred mode for practicing the present invention, it will be apparent to those skilled in the art that the above-described approach can vary in accordance with techniques known in the art.

c. Methods for Enhancing Expression

Once the desired restriction endonuclease and modification methylase genes have been isolated, a number of recombinant DNA strategies exist for enhanced production of the desired proteins in these hosts. These strategies which will be appreciated by those skilled in the art, utilize high copy number cloning vectors or expression vectors.

Furthermore, those skilled in the art will recognize that both the restriction endonuclease and modification methylase genes need not be maintained on the same cloning or expression vector within the same recombinant host. The endonuclease gene, for example, may be located on one vector, while its corresponding methylase gene may be located on a separate vector or located on the host genome. Various combinations of maintaining both the modification and restriction genes within the same recombinant host can be constructed. The only requirement, when cloning restriction endonuclease genes, is that the recombinant host contain and express the methylase gene corresponding to the endonuclease gene being cloned.

In order to enhance the production of the desired restriction endonuclease in a prokaryotic cell, it is important to maintain expression of the corresponding modification methylase gene sufficient to protect the DNA of the recombinant host against cleavage with the cloned restriction endonuclease. Therefore, it may be necessary to enhance the level of methylase expression in conjunction with increased endonuclease activity.

Enhanced production of these enzymes can be accomplished, for example, by operably linking the desired gene(s) to a strong prokaryotic promoter. Such promoters may be either constitutive or, more preferably, regulatable (i.e., inducible or derepressible). Examples of constitutive promoters include the int promoter of bacteriophage λ, and the bla promoter of the β-lactamase gene of pBR322, etc. Examples of inducible prokaryotic promoters include the major left and right promoters of bacteriophage λ ($P_L$ and $P_R$), the trp. recA. lacZ. gal. and tac promoters of *E. coli.* the α-amylase (Ulmanen, I., et al., *J. Bacteriol.* 162:176–182 (1985)), the α-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., N.Y. (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)). In is important to note that the restriction endonuclease gene may be cloned in a host which is not protected with the methylase gene, provided that the endonuclease gene is operably linked to a controllable promoter.

Proper expression in a prokaryotic cell also requires the presence of a ribosome binding site upstream from the gene-encoding sequence. Such ribosome binding sites are disclosed, for example, by Gold, L., et al. (*Ann. Rev. Microbiol.* 35:365–404 (1981)).

III. Isolation and Purification of the Restriction Endonucleases and Modification Methylase Enzymes from Recombinant Hosts The enzymes of this invention (NgoAIII, M.NgoAIII, NgoAI, M.NgoAI, and M.NgoAII) or isoschizomers thereof are preferably produced by fermentation of the recombinant host containing and expressing the cloned restriction endonuclease and/or modification methylase genes. The recombinant host, such as *E. coli* producing the cloned proteins, can be grown and harvested according to techniques well known in the art.

Any nutrients that can be assimilated by the host containing the cloned restriction endonuclease and modification methylase genes may be added to the culture medium. Glucose, sucrose, maltose, lactose, glycerol, ethanol, lactates, various fats and oils, and others may be used as carbon source, while yeast extract, peptone, defatted soybeans, corn steep liquor, bouillon and others are suitable as nitrogen source. Minerals and metal salts, e.g., phosphates, potassium salts and magnesium salts, iron, as well as vitamins and growth-promoting substances, may also be added as required.

Optimal culture conditions should be selected case by case according to the strain used and the composition of the culture medium. Restriction endonucleases and modification methylases produced by the recombinant hosts of this invention are accumulated inside the microbial cells.

The recombinant host cells producing the restriction endonuclease and/or modification methylase of this invention can be separated from the culture liquid, for example, by centrifugation. Both of these enzymes can be extracted and purified by using known protein purification techniques commonly employed for these types of enzymes.

In general, the collected microbial cells are dispersed in a suitable buffer, and then broken down by ultrasonic treatment to allow extraction of the enzyme by the buffer solution. After removal of the residue by ultracentrifugation, ammonium sulfate can be added to the supernatant of the crude lysate for salting out, and the precipitate which separates out is dissolved in a Tris-HCl buffer (pH: 7.6) and dialyzed against a buffer of the same composition. The dialyzed sample can be purified by ion-exchange chromatography, molecular-sieve chromatography and affinity chromatography, giving the restriction endonuclease or modification methylase of this invention.

In an example to purify NgoAIII from a recombinant host expressing the genes encoding the restriction-modification system of NgoAIII, the crude lysate is absorbed directly onto a heparin-agarose (BRL) column, followed by elution with 0.05 to 0.6M NaCl solutions. The active fractions are then pooled and dialyzed to reduce the NaCl concentration to 0.02 M. The dialyzed material containing the active enzyme is then bound to a MONO-Q column (Pharmacia), followed by elution with 0 to 0.4 M NaCl solutions. The active fractions collected are then dilated 1:1 with buffer lacking NaCl and absorbed to a MONO-S column (Parmacia) which is eluted with 0.05 to 0.6 M NaCl solutions. The active peak fractions are made 50% (V/V) in glycerol affording a standard sample of NgoAIII.

According to the present invention, assays to detect the presence of the restriction endonucleases and modification methylases can be used during the conventional biochemical purification methods to determine the presence of these enzymes.

Restriction endonuclease can be identified on the basis of the cleavage of its recognition sequence. As substrate, there can be used, for example, Adenovirus-2 (Ad-2) DNA. The DNA fragments obtained are separated electrophoretically in agarose gels in the buffer systems conventional for the fragment separation in the presence of ethidium bromide.

Demonstration of modification methylase activity can be, but is not limited to, a two-step identification process. First, DNA substrate (Ad-2 DNA) that contains the recognition sequence is incubated with column fractions to be tested for methylase activity. Secondly, this DNA is then challenged with the corresponding restriction activity to identify those fractions which contain methylase activity. For example, while assaying for M.NgoAIII, the DNA samples will be challenged with NgoAIII. Thus, DNA samples which do not exhibit cleavage with NgoAIII contain M.NgoAIII activity.

The recombinant host containing the genes encoding for NgoAIII and M.NgoAIII (designated DHIOB/pRMNgoAIII) was put on deposit with the Patent Culture Collection, Northern Regional Research Center, USDA, 1815 N. University Street, Peoria, Ill. 61604 USA (NRRL) as deposit no. NRRL B-18657.

The recombinant host containing the genes encoding for NgoAI and M.NgoAI (designated DH5αMCR/pRMNgoAI) was put on deposit with the NRRL as deposit no. NRRL B-18656.

EXAMPLE 1

Bacterial Strains and Growth Conditions

*Neisseria gonorrhoeae* FA1090 (provided by Dr. M. S. Cohen, University of North Carolina, Chapel Hill) was grown at 37° C. in the presence of 5% (v/v) $CO_2$ in CTA medium (1.125% [w/v] Protease Peptone No. 3; 1% [w/v] nutrient agar; 0.1% [w/v] $KH_2PO_4$; 0.4% [w/v] $K_2HPO_4$; 0.5% w/v] NaCl; 0.1% [w/v] soluble starch; and 1% [v/v] of a solution containing 40% [w/v] glucose; 0.5% [w/v] L-glutamine; 0.05% [w/v] $Fe(NO_3)_3$; 0.002% [w/v] thiamine pyrophosphate). The cells were centrifuged and stored at −70° C. as a cell pellet prior to total genomic DNA isolation.

*E. coli* strains were grown at 37° C. in YET broth (10 g/l Bacto trypton, 5 g/l yeast extract and 5 g/l NaCL) with antibiotic supplements of ampicillin (Ap), 100 µg/ml; or tetracycline (Tc), 20 µg/ml as required. *E. coli* strains, K802 (Maniatis et al.: Molecular cloning. A Laboratory Manual, Cold Spring Harbor Laboratory, Cold Spring Harbor, N.Y., 1982), DH5αMCR, or DH10B were used interchangeably for cloning the restriction modification genes from *Neisseria gonorrhoeae*. DH5αMCR and DH10B competent cells were obtain commercially from Life Technologies Inc. (LTI), Gaithersburg, Md. Competent cells of K802 were made by a protocol previously described (Hanahan, D., J. Mol. Biol. 51:557–580 (1983)).

EXAMPLE 2

DNA Isolation

Small scale plasmid DNA isolations were performed by an alkaline lysis method (Maniatis et al., 1982). For large scale preparations, alkaline lysis was followed by standard CsCl-EtdBr gradient centrifugation (Maniatis et al., 1982).

*Neisseria gonorrhoeae* total genomic DNA was isolated by resuspending 2 grams of frozen cells in 8 mls of TNE buffer (50 mM Tris-HCl pH 8.0, 50 mM NaCl and 10 mM EDTA). A 10 mg/ml lysozyme solution in TNE buffer was added to the cell suspension to a final concentration of 1 mg/ml. After a one hour incubation at 37° C., 10% SDS was added to a 2% final concentration and the suspension was shaken gently until lysis was complete. After cell lysis, the lysate was extracted once with phenol and twice with phenol:chloroform:isoamylalcohol (1:24:1). DNA was spooled with a glass rod under two volumes of cold ethanol (−20° C.), dissolved in TE (10 mM Tris-HCl pH 8.0, and mM EDTA) and purified by CsCl-EtdBr gradient centrifugation.

EXAMPLE 3

Construction of Genomic Libraries

Genomic DNA of *Neisseria gonorrhoeae* was digested partially with HpaII as follows: Purified genomic DNA was digested with HpaII in a 10 µl volume with 0.42, 0.21, 0.105, 0.0525, 0.026 or 0.013 u/µg. Each digestion reaction contained 0.3 µg of DNA in 20 mM Tris-HCl (pH 7.4), and 10 mM $MgCl_2$. After the samples were incubated one hour at 37° C., the DNA was analyzed by agarose gel electrophoresis.

Conditions required to achieve minimal digestion (90% of the DNA greater than 15 Kb in length) were chosen as determined by gel electrophoresis. Enzyme concentrations of 0.105 and 0.0525 u/µg provided the conditions necessary for minimal digestion of the genomic DNA. These reactions were subsequently scaled up 10 fold.

Two tubes, each containing 3 µg of genomic DNA, were partially digested in a 100 µl reaction volume as described above with 0.105 or 0.0525 u/µg of HpaII. After incubation, a 20 µl sample of each was analyzed by agarose gel electrophoresis to confirm minimal digestion of the scaled up reactions. The fragmented DNA from these reactions were combined, extracted with phenylchloroform, ethanol precipitated, and dissolved in 10 µl of TE buffer.

One µg of ClaI cleaved and dephosphorylated pCP13 vector was ligated with 2 µg of the partially digested genomic DNA using two units of T4 DNA ligase in 1×ligase buffer (0.05 M Tris-HCl (pH 7.6), 10 mM $MgCl_2$, 1 mM ATP, 1 mM DTT, and 5% (w/v) polyethylene glycol-8000). The 20 µl ligation reaction was incubated at room temperature (25° C.) overnight.

Approximately 0.75 µg of ligated DNA (5 µl of the ligation reaction mixture) was packaged using Stratagene's Gigapack Gold Lambda Packaging System according to the manufactures recommended procedure. After the packaging reaction was complete, *E. coli* cells were infected with the packaging mix as follows: DH5αMCR cells were prepared by growing an overnight culture in YET media containing 0.2% maltose. The next day, 500 µls of these cells were inoculated into 10 mls of YET containing 0.2% maltose and grown to mid-log phase. These cells were then centrifuged and resuspended in 4.0 mls of sterile 10 mM $MgSO_4$ buffer. 200 µls of the cell suspension was mixed with 100 µls of packaging mix. After a 30 minute incubation at 37° C. without shaking, a 700 µl volume of SOC media (2% Bacto tryptone, 0.5% Yeast extract, 10 mM NaCl, 2.5 mM KCl, 10 mM MgCl$_2$, 10 mM MgSO$_4$ and 20 mM glucose) was added. The cells were allowed to grow at 37° C. in an air shaker-incubator for 30 minutes. The cells were then plated onto 9 YET agar plates containing tetracycline and incubated overnight.

Approximately $5 \times 10^4$ tetracycline resistant colonies were pooled together by scraping the cells from the agar surface. This was accomplished by flooding each plate with 2.5 mls of filter sterilized PEB I (50 mM glucose, 25 mM Tris-HCl pH 8.0 and 10 mM EDTA). After carefully resuspending the cells in buffer with a sterilized glass rod, the cell suspension was transferred to a sterile tube and stored at $-70°$ C. Before freezing these cells, a 5 ml aliquot was removed and immediately inoculated into I liter of YET media containing tetracycline.

After a five hour growth, the cells were harvested, resuspended in 100 mls of PEB I and then combined with the pooled cells which were previously stored at $-70°$ C. Plasmid DNA was isolated from this cell suspension according to Example 2. The isolated cosmid library was designated *Neisseria gonorrhoeae* plasmid library.

EXAMPLE 4

Selection of Clones Expressing Methylase and Restriction Enzymes

Clones expressing M.NgoIII, M.NgoAI or M.NgoAII methylase were selected by digesting the cosmid library with an excess amount of SstII, HaeII or HaeIII, respectively. To select M.NgOAIII, *Neisseria gonorrhoeae* plasmid library (5 µg) was digested in a reaction volume of a 100 µl containing 1 X REact 2 buffer (50 mM Tris-HCl pH 8.0, and 10 mM MgCl$_2$, 50mM NaCl) with 70 units of SstII at 37° C. for 4.5 hours. One half of the digested DNA was dephosphorylated by adding 2 units of calf intestinal alkaline phosphatase (supplied by Boehringer Mannheim) to 50 µls of the reaction mix. After a 1 hour incubation at 37° C., the DNA was extracted with an equal volume of phenol:chloroform (1:1), ethanol precipitated, and resuspended in 10 µl of TE buffer.

M.NgoAI and M NgoAII methylase clones were selected by digesting *Neisseria gonorrhoeae* plasmid library by following the general procedure used to select M.NgoAIII except that 70 units of HaeII was used to select recombinant hosts expressing M.NgoAI and 35 units of HaeIII was used to select clones expressing M.NgoAII.

*E. coli* DH5αMCR competent cells were transformed with the digested DNA library according to the manufacturers suggested protocol. Briefly, 100 µls of cold competent cells were mixed with the 10 µl sample of the SstII, HaeII or HaeIII digested DNA. The cells were incubated without shaking for 30 minutes on ice. After a 45 second heat shock at 42° C., the cells were diluted with 900 µl of SOC and grown for 30 minutes at 37° C. Approximately 100–300 tetracycline resistant colonies were isolated after plating the transformed cells on YET agar plates containing tetracycline.

Colonies that survived the methylase selection scheme were analyzed for the presence of methylase activity. Thirty clones, ten clones each that survived SstII, HaeII or HaeIII selection, were individually inoculated and grown overnight in 2 mls of YET media containing tetracycline. Small scale plasmid isolations were preformed as previously described. DNA preparations isolated from clones which survived SstII, HaeII or HaeIII digestion were then tested for their ability to resist cleavage with SstII, HaeII or HaeIII, respectively, as follows:

A 0.5 to 1.0 µg amount of isolated DNA was digested in 1 X REact 2 buffer with 10 units of the appropriate restriction endonuclease at 37° C. for hour in a 20 µl reaction. Protection of the resident plasmid and the host chromosomal DNA from digestion indicated the presence of methylase activity. Analysis of all clones isolated by agarose gel electrophoresis demonstrated that neither the host chromosomal DNA nor the resident plasmid DNA of these clones were cleaved by their respective enzymes. Two clones from each group were saved and later assayed for restriction enzyme activity according to Example 5. These clones were designated numerically: 61 and 62-recombinant hosts which express M.NgoAIII, selected with SstII; 25 and 26-recombinant hosts which express M.NgoAI, selected with HaeII; and 35 and 37-recombinant hosts which express M.NgoAII, selected with HaeIII.

Recombinant hosts (61, 62, 25, 26, 35, and 37) were tested for restriction endonuclease activity according to Example 5. All recombinant hosts except 26, 35 and 37 exhibited expression of restriction endonuclease activity. Thus, clones 61 and 62 expressed the genes encoding for M.NgoAIII and NgoAIII while clone 25 expressed the genes encoding for M.NgoAI and NgoAI. Recombinant hosts 35 and 37 appeared to express M.NgoAII activity without any detectable restriction endonuclease activity.

EXAMPLE 5

Assay for Restriction Enzyme Activity

A 20 ml overnight culture was harvested and resuspended in 1 ml buffer containing 10 mM Tris-HCl (pH 7.5), 10 mM beta-mercaptoethanol and 1 mM EDTA. Cells were sonicated on ice by 3 to 4, 10 second blast with a microtip probe. After sonication, the cell extract was centrifuged at 4° C. for 30 sec. using a microfuge (1.5 ml tubes) in order to separate the cell debris.

Adenovirus-2 (Ad-2) DNA substrate (0.75 µg) was digested in 1×REact 2 buffer with serial dilutions of extract as follows: Ad-2 DNA was diluted to a concentration of 0.038 µg/ul in 1×REact 2 buffer. A 30 µl aliquot of the sample DNA was then added to the first tube and 20 µl aliquots were dispensed into the second, third and fourth tubes. A 3 µl volume of crude extract was mixed into the first tube. A 10 µl sample was then removed and serially diluted into the remaining tubes, with the final tube having the highest dilution of extract. The samples were incubated at 37° C. for 1 hour and a 20 µl aliquot was analyzed by agarose gel electrophoresis.

EXAMPLE 6

Over Expression of the M.NgoAII Modification Methylase

To enhance expression M.NgoAII methylase, the gene encoding for M.NgoAII was cloned into a high copy number vector, pUC19 (Yanisch-Perron, C. et al., *Gene* 33:103–119(1985)). Plasmid DNA was isolated from clone 35 using the small scale isolation procedure. Approximately 1 µg of this DNA was digested for 1 hour with 100 units of EcoRI in 100 µl of 1×REact 3 buffer (50 mM Tris-HCL pH 8.0, 10 mM MgCl$_2$ and 0.1

M NaCl) at 37° C. After incubation, the reaction mixture was extracted with phenylchloroform, ethanol precipitated and dissolved in TE buffer.

Approximately 0.5 μg of EcoRI cleaved and dephosphorylated pBR322 vector (Bolivar F. et al *Gene* 2:95-113 (1977)) was ligated with 0.5 μg of EcoRI digested plasmid DNA from clone 35. The ligation mixture was incubated at room temperature overnight in a 20 μl reaction containing x ligase buffer and 2 units of T4 DNA ligase enzyme.

Competent K802 cells were transformed with 3 μl of the ligation mixture according to the protocol described in Example 4. After the 30 minutes expression step, the cells were plated on YET plates containing ampicillin and incubated overnight.

The next day, approximately $1 \times 10^3$ Ap resistant cells were pooled together by scraping the cells from the outer surface as described in Example 3. A 100 μl volume of the cell suspension was removed and a standard small scale plasmid purification was performed. The isolated DNA was then digested with 80 u/μg of HaeIII in 100 μl of 1×REact 2 buffer. The sample was dephosphorylated with 2 units of calf intestinal alkaline phosphatase at 37° C. for 1 hour, extracted, ethanol precipitated and taken up in 10 μl of TE. 100 μls of cold competent *E. coli* K802 cells were transformed with 5 μl of this DNA sample. The cells were then diluted and plated on YET agar plates containing ampicillin.

The next day, single colony isolates were screened for methylase activity as in example 4. A recombinant clone was isolated which contained and expressed the M.NgoAII gene on a greater than 15 kb EcoRI fragment inserted into pBR322. This intermediate clone was subsequently used to isolate an approximately 4.0 kb AvaI DNA fragment from the 15 Kb EcoRI fragment. This 4.0 kb AvaI DNA fragment was ligated into the AvaI site in pUC19 and then transformed into DH5αMCR. The recombinant host containing pUC19 with a 4.0 kb AvaI insert exhibited high levels of M.NgoAII methylase activity. This strain was designated DH5αMCR/pMNgoAII.

EXAMPLE 7

Over Expression of the M.NgoAIII and NgoAIII Restriction Endonuclease

To enhance the expression of NgoAIII methylase and restriction enzymes, the genes encoding for M.NgoAIII and NgoAII were cloned into a high copy number plasmid pUC19 (see Example 6). Plasmid DNA from clone 61 (Example 4) was used for the overexpression of NgoAIII restriction-modification system. Approximately 1 μg of this plasmid was digested with XhoI by a standard protocol suggested by the manufacture, extracted with phenol:chloroform/isoamyl alcohol (1:1) and ethanol precipitated. The XhoI digested DNA was then self-ligated and the ligated DNA transformed into DHIOB. The rationale of XhoI digestion and self-ligation was to eliminate extra portion of the unwanted DNA but to leave the genes coding for the NgoAIII restriction-modification enzymes. Indeed, the XhoI fragment deletion resulted in clones containing much smaller (approximately 4.4 kb DNA compared to about 30 kb portion of *N. gonorrhoeae* DNA in the original clone 61). The resulting clone designating 61X3 produced both NgoAIII methylase and restriction enzyme. A linear approximate map of plasmid DNA in 61X3 is shown in FIG. 1.

To subclone the remaining portion of *N. gonorrhoeae* DNA containing genes for M.NgoAIII and NgoAIII, the 61X3 plasmid DNA was digested with BamHI and EcoRI and a 2.8 kb fragment was purified and ligated into pUC19 at BamHI-EcoRI sites. Note that the BamHI site was derived from the vector pCP13. The ligated DNA was introduced into a protected host, DHIOB containing plasmid DNA from 61X3. The transformants were selected with both ampicillin and tetracycline antibiotics in the presence of XGal. All white clones contained the desired 2.8 kb fragment. Finally, a 1.6 kb EcoRI fragment was reconstructed at the EcoRI site of pUC19-2.8 kb plasmid. Two types of NgoAIII activities were noticed; clones with about 5 times more activity than others. Presumably, this difference was due to the different orientation of the EcoRI fragment in the final construct. However, no attempts were made to confirm the speculation. The clones with the highest activities were saved. One of the clones was designated as DHIOB/pRMNgoAIII.

Figure 2:
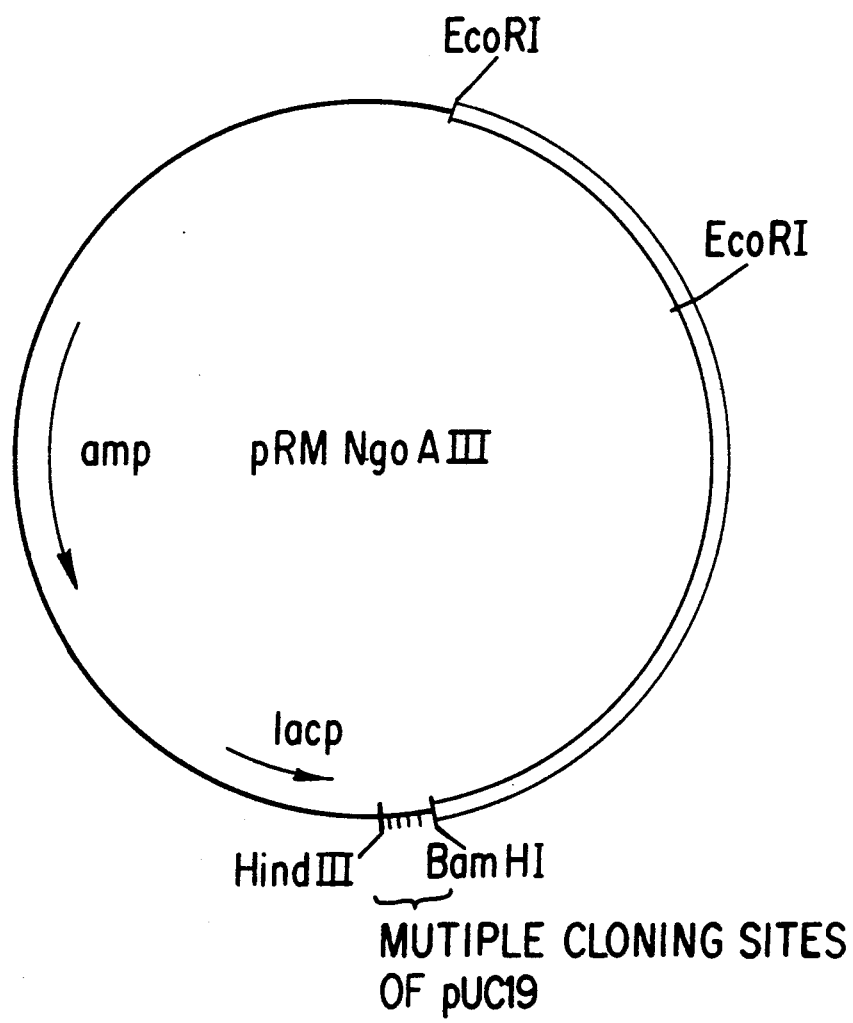
FIG. 2 shows a simplified restriction map of plasmid DNA, pRMNgoAIII. This plasmid contains and expresses the genes which encode for NgoAIII and M.NgoAIII.

A simplified restriction map of plasmid DNA, pRMNgoAIII, is shown in FIG. 2. The map was established by a standard mapping protocol.

EXAMPLE 8

Purification of NgoAIII Restriction Endonuclease

NgoAIII restriction enzyme was purified from the overproducing recombinant host, DHIOB/pRMNgoAIII. Approximately 100,000 units of purified enzyme can be obtained from 3.3 grams of cells by following the procedure described below.

In an example to purify NgoAIII from a recombinant host expressing the genes encoding the restriction-modification system of NgoAIII, the crude lysate is absorbed directly onto a heparin-agarose (BRL) column, followed by elution with 0.05 to 0.6M NaCl solutions. The active fractions are then pooled and dialyzed to reduce the NaCl concentration to 0.02 M. The dialyzed material containing the active enzyme is then bound to a MONO-Q column (Pharmacia), followed by elution with 0 to 0.4 M NaCl solutions. The active fractions collected are then dialyzed 1:1 with buffer lacking NaCl and absorbed to a MONO-S column (Parmacia) which is eluted with 0.05 to 0.6 M NaCl solutions. The active peak fractions are made 50% (V/V) in glycerol, affording a standard sample of NgoAIII.

EXAMPLE 9

Characterization of the NgoAIII Restriction Endonuclease

The NgoAIII restriction enzyme purified in example 8 was characterized to determine its nucleotide recognition sequence as well as the location of cleavage within this recognition site. As detailed below, NgoAIII was determined to be a type II restriction endonuclease, which recognizes the sequence 5'CCGC↓GG3' producing a 2-base 3'-extension.

The fragments generated after the cleavage of Ad-2 DNA by NgoAIII were identical to the fragment profile obtained when Ad-2 DNA is cleaved with SstII, which recognizes the same sequence. Therefore, the cleavage site of NgoAIII was determined and compared with that of SstII.

The position of phosphodiester bond cleavage within the recognition site was determined by the method of Brown and Smith (Brown, N.L. et al., *Methods Enzymol.* 65:391–404 (1980)). Sequencing reactions were performed as described by Sanger, et al. (*J. Mol. Biol.* 143:161–178 (1980)). A DNA fragment containing an SstII site was introduced into M13mp19 for cleavage-site determination. Single-stranded DNA template containing the SStII site was used to synthesize double-stranded DNA through the SstII site using BRL universal primer. The extended DNA was cleaved with NgoAIII and SstII separately. Aliquots of the digested products were run on a sequencing gel next to DNA sequencing reaction products produced with the same template and primer. The results showed that both NgoAIII and SstII produced a fragment which comigrated with the 3'C within the recognition sequence 5'CCGCGG3'. Treatment with Klenow fragment or T4 DNA polymerase in the presence of all four deoxyribonucleotides, subsequent to NgoAIII or SstII digestion, shifted the migration of the fragments to a position corresponding to the second 5'C. These results demonstrate that both NgoAIII and SstII cleave at the same site within the sequence. In addition, Ad-2 DNA fragments generated by NgoAIII digestion can be cloned into a SstII-cleaved vector and all cloned fragments are recovered by digestion with either SstII or NgoAIII. These results demonstrate that NgoAIII cleaves between the second C and G from the 5' end to produce a 2-base 3' extension:

5'CCGC ↓ GG3'

3'GG ↑ CGCC5'

What is claimed is:

1. A recombinant host expressing a gene encoding for a restriction endonuclease, said restriction endonuclease recognizing the palindromic sequence:

5' CCGC ↓ GG 3'

3'GG ↑ CGCC 5' and cleaving said sequence between the second C and G residues form the 5' end, producing a two-base 3' extension, wherein said gene is obtainable from the recombinant host on deposit with the Patent Culture Collection, Northern Regional Research Center, USDA, under deposit no. NRRL B-18657.

2. The recombinant host of claim 1, wherein said gene is obtained from the genus Neisseria.

3. The recombinant host of claim 1, wherein said gene obtained from *Neisseria gonorrhoeae.*

4. The recombinant host of claim 1, wherein said gene encodes for NgoAIII.

5. A recombinant vector containing the gene of any one of claims 1 to 4, wherein said gene encodes for a restriction endonuclease, said restriction endonuclease recognizing the palindromic sequence:

5'CCGC ↓ GG 3'

3'GG ↑ CGCC 5' and cleaving said sequence between the second C and G residues from the 5'end, producing a two-base 3' extension.

6. The recombinant vector of claim 5, wherein said recombinant vector also contains a gene encoding for a modification methylase, said modification methylase recognizing and chemically modifying the palindromic sequence:

5'CCGCGG 3'

3'GGCGCC 5' such that said modified sequence is resistant to cleavage with its corresponding restriction endonuclease, wherein said gene encoding for said modification methylase is obtainable from the recombinant host on deposit with the Patent Culture Collection, Northern Regional Research Center, USDA, under deposit no. NRRL B-18657.

7. A recombinant host expressing a gene encoding for a modification methylase recognizing and chemically modifying the palindromic sequence:

5'CCGCGG 3'

3'GGCGCC 5' such that said modified sequence is resistant to cleavage with its corresponding restriction endonuclease, wherein said gene encoding for said modification methylase is obtainable from the recombinant host on deposit with the Patent Culture Collection, Northern Regional Research Center, USDA, under deposit no. NRRL B-18657.

8. The recombinant host of claim 7, wherein said gene is obtained from *Neisseria gonorrhoeae.*

9. The recombinant host of claim 7, wherein said gene encodes for M.NgoAIII.

10. A recombinant vector containing the gene of any one of claims 7 and 9, wherein said gene encodes for a modification methylase, said modification methylase recognizing and chemically modifying the palindromic sequence:

5'CCGCGG 3'

3'GGCGCC 5' such that said modified sequence is resistant to cleavage with its corresponding restriction endonuclease.

* * * * *